United States Patent
Zhang et al.

(10) Patent No.: US 9,219,178 B2
(45) Date of Patent: Dec. 22, 2015

(54) METHOD TO FABRICATE COLLIMATOR STRUCTURES ON A DIRECT CONVERSION SEMICONDUCTOR X-RAY DETECTOR

(71) Applicants: KABUSHIKI KAISHA TOSHIBA, Tokyo (JP); TOSHIBA MEDICAL SYSTEMS CORPORATION, Tochigi (JP)

(72) Inventors: Yuexing Zhang, Naperville, IL (US); Daniel Gagnon, Twinsburg, OH (US); Xiaolan Wang, Buffalo Grove, IL (US)

(73) Assignees: KABUSHIKI KAISHA TOSHIBA, Tokyo (JP); TOSHIBA MEDICAL SYSTEMS CORPORATION, Tochigi (JP)

( * ) Notice: Subject to any disclaimer, the term of this patent is extended or adjusted under 35 U.S.C. 154(b) by 89 days.

(21) Appl. No.: 14/222,226

(22) Filed: Mar. 21, 2014

(65) Prior Publication Data

US 2015/0270413 A1    Sep. 24, 2015

(51) Int. Cl.
| | |
|---|---|
| *H01L 21/00* | (2006.01) |
| *H01L 31/0232* | (2014.01) |
| *G21K 1/02* | (2006.01) |
| *G21K 1/10* | (2006.01) |
| *A61B 6/00* | (2006.01) |

(52) U.S. Cl.
CPC .......... *H01L 31/02327* (2013.01); *A61B 6/502* (2013.01); *G21K 1/025* (2013.01); *G21K 1/10* (2013.01)

(58) Field of Classification Search
CPC .... H01L 31/02327; G21K 1/025; G21K 1/10; A61B 6/502
See application file for complete search history.

(56) References Cited

U.S. PATENT DOCUMENTS

| | | | |
|---|---|---|---|
| 3,957,552 A * | 5/1976 | Ahn et al. | 430/312 |
| 4,088,490 A * | 5/1978 | Duke et al. | 430/312 |
| 5,814,235 A * | 9/1998 | Pellegrino et al. | 216/12 |
| 6,980,629 B1 * | 12/2005 | Hoheisel et al. | 378/149 |
| 2005/0001170 A1 * | 1/2005 | Juni | 250/363.04 |
| 2013/0026380 A1 * | 1/2013 | Tkaczyk et al. | 250/370.13 |

* cited by examiner

*Primary Examiner* — Stephen W Smoot
*Assistant Examiner* — Vicki B Booker
(74) *Attorney, Agent, or Firm* — Oblon, McClelland, Maier & Neustadt, L.L.P.

(57) ABSTRACT

A method of fabrication of a collimator structure on a detector that includes applying a first layer of resist to a semiconductor sensor, applying a second layer of resist over the first layer of resist and the semiconductor sensor to cover both the first layer of resist and the semiconductor sensor, exposing the second layer of resist to ultraviolet (UV) light with a photomask to transfer a pattern from the photomask to the second layer of resist, removing portions of the second layer of resist corresponding to the pattern from the photomask to produce openings in the second layer of resist, which expose upper portions of the semiconductor sensor, and depositing a layer of metal in the openings and on the second layer of resist to cover the openings, the first layer of resist, the second layer of resist, and the semiconductor sensor.

10 Claims, 11 Drawing Sheets

METHOD TO FABRICATE COLLIMATOR STRUCTURES ON A DIRECT CONVERSION SEMICONDUCTOR X-RAY DETECTOR

BACKGROUND

1. Field

Embodiments described herein relate to collimator structures and the fabrication thereof for photon-counting detectors.

2. Background

In a semiconductor-based, photon-counting Computed Tomography (CT) apparatus, to prevent polarization (hole build-up in semiconductor sensor) and electronics pile-up, a detector side collimator with small slit-shape openings is needed. Further, the collimator needs to properly align with detector pixels. The manufacturing and alignment of such collimators present a great challenge in the field.

BRIEF DESCRIPTION OF THE DRAWINGS

The disclosure will be better understood from reading the description which follows and from examining the accompanying figures. These figures are provided solely as non-limiting examples of the embodiments. In the drawings:

FIGS. 4 (4A, 4B, and 4C) illustrates an end view, a top view, and a side view of a pixelated cadmium zinc telluride (CZT) sensor.

DETAILED DESCRIPTION

In one embodiment, there is provided a method of fabrication of a collimator structure on a detector of a Computed Tomography (CT) apparatus. The method comprising applying a first layer of resist to a semiconductor sensor; applying a second layer of resist over the first layer of resist and the semiconductor sensor to cover both the first layer of resist and the semiconductor sensor; exposing the second layer of resist to ultraviolet (UV) light with a photomask to transfer a pattern from the photomask to the second layer of resist; removing portions of the second layer of resist corresponding to the pattern from the photomask to produce openings in the second layer of resist, which expose upper portions of the semiconductor sensor; depositing a layer of metal in the openings and on the second layer of resist to cover the openings, the first layer of resist, the second layer of resist, and the semiconductor sensor; polishing an upper portion of the layer of metal such that the layer of metal in the openings is flush with the second layer of resist; and dicing the first layer of resist and the second layer of resist.

In one embodiment, the depositing step includes depositing a second layer of metal to cover the layer of metal.

In one embodiment, the layer of metal is of a lower attenuation than the second layer of metal.

In one embodiment, the layer of metal is of one of lead (Pb), tungsten (W), and molybdenum (Mo).

In one embodiment, the first layer of resist is an SU-8 resist. In one embodiment, the second layer of resist is an SU-8 resist.

In one embodiment, the method further comprises performing flood exposure of the first layer of resist, before the applying of the second layer of resist.

In one embodiment, the method further comprises curing the first layer of resist, after the performing of the flood exposure and before the applying of the second layer of resist.

In one embodiment, the method further comprises curing the first layer of resist and the second layer of resist, after the removing of the portions of the second layer of resist.

In one embodiment, the semiconductor sensor is one of a cadmium zinc telluride (CZT) sensor, a cadmium telluride (CdTe) sensor, and a mercury iodide (HgI) sensor.

Figure 1:
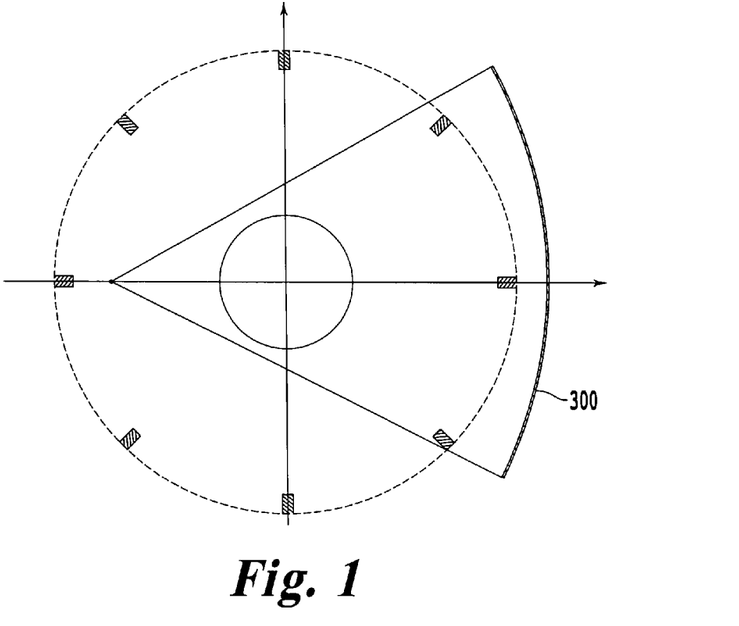
FIG. 1 illustrates a CT imaging system of a CT apparatus.

FIG. 1 illustrates a sparse spectral CT imaging system that includes stationary, sparse photon-counting detectors (PCDs) and a rotating X-ray source. The source trajectory may be inside or outside the ring defined by the PCDs.

Figure 2:
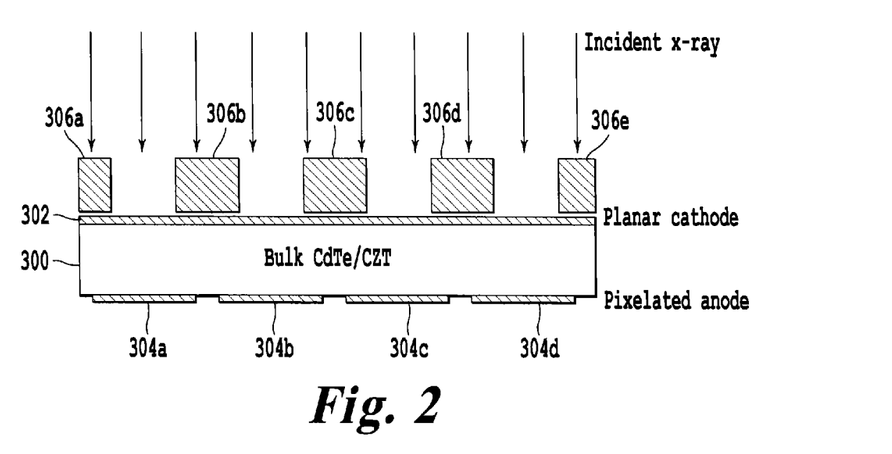
FIG. 2 illustrates an exemplary embodiment of a photon-counting detector (PCD) with collimators.

FIG. 2 illustrates one embodiment of a PCD with collimators. As illustrated in FIG. 2, PCD 300 includes pixelated anodes 304a to 304d and planar cathode 302. In one embodiment, each of pixelated anodes 304a-304d corresponds to individual pixels. In some embodiments, the PCD 300 is a semiconductor PCD made of a continuous bulk material such as cadmium telluride (CdTe) or cadmium zinc telluride (CZT). In one embodiment, PCD 300 may be made of mercury iodide (HgI). As illustrated in FIG. 2, collimators 306a-306e are positioned on the cathode side of the PCD 300. In some embodiments, the collimators 306a to 306e are provided on the edges of each pixel. In this regard, the collimators block out (most, but not all) incident X-rays from hitting the edges of the pixels so that only the centers of the pixels 304a-304d receive the incident X-rays.

Accordingly, as illustrated in FIG. 2, the installed collimators 306a-306e separate individual detector channels/pixels. In one embodiment, each of the collimators 306a-306e is part of a mask that is overlaid on the cathode side of the PCD. In another embodiment, 10%-60% of each of the full pixel or the whole cathode is covered by the collimators, depending on the amount of flux incident on the PCD.

The present disclosure describes a method to fabricate a collimator structure (such as the one shown in FIG. 2), with proper attenuation and collimation properties, with good alignment with the detector pixels, and with a shape appropriate for X-ray incidence from different detector fan angles (DETF).

In one embodiment, a photolithography method is used to pattern heavy materials (e.g., lead (Pb), tungsten (W), molybdenum (Mo), or multiple layers of different materials) and low attenuation polymer materials (such as SU-8 photoresist) to form a collimator structure over the CZT sensor cathode side. Creating metal layers, especially multiple layers, is difficult for classical machining techniques.

In one embodiment, a photolithography method is used to pattern non-metal materials. By using a non-metal material, it is possible to build an optical filter (such as a bandgap filter) instead of a collimator.

SU-8 is a commonly used epoxy-based negative-tone resist well suited for high aspect ratio structures. SU-8 has a low attenuation for X-rays (<4% for 2 mm, a typical height in the proposed designs), and is mechanically strong and stable.

In one embodiment, the polymer material, SU-8, remains as part of the structure, between metal, and surrounds the metal collimator piece and the detector crystal (e.g., CZT). This method can form "overhangs" or partially wrapped-around structures to enable collimation at the sides of the detector (for incident beams at a "polar angle"). The "overhangs" (part of, for example, layers 900 and 500) can be seen in numerous figures, including FIG. 12A. In one embodiment, the fabrication method can process batches of detectors at the same time.

In one embodiment, the method of fabrication of collimator structures on a direct conversion detector (such as PCD 300 shown in FIG. 2) can be summarized as follows. First, two layers of SU-8 photoresist are patterned with lithography. Next, one or multiple layers of heavy metal are deposited (sputtered or evaporated). Third, the surface is polished to remove excess metal layer(s) and SU-8. Finally, the sides are diced (or wire cut) to achieve the desired shape. The desired shape may be, for example, a rectangular shape.

Figure 3:
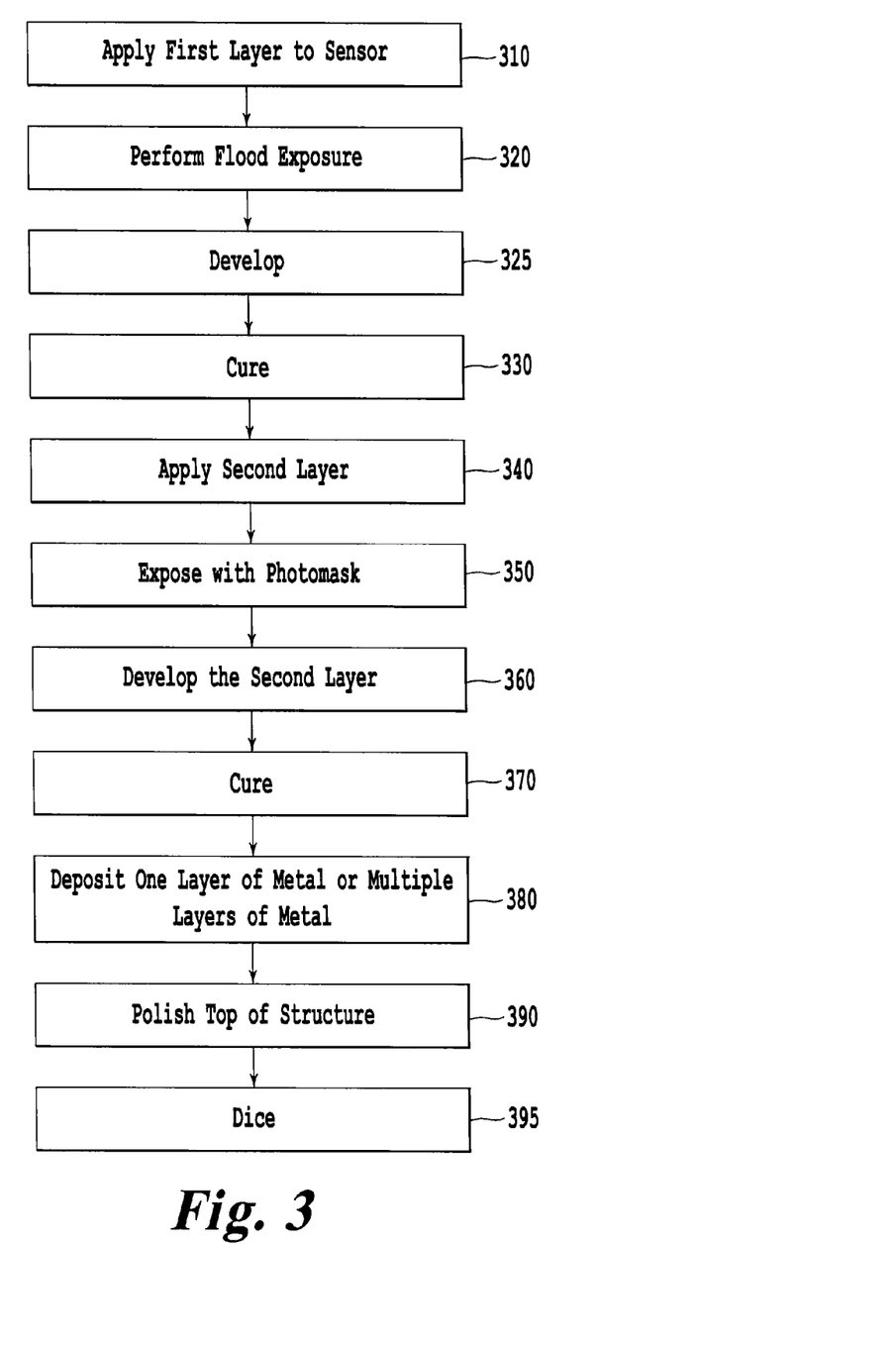
FIG. 3 is a flowchart of a method of fabrication of a collimator structure.

FIG. 3 shows the method of fabrication of the collimator structure. The method of FIG. 3 can be applied to a CZT sensor or to any solid state detector. The method illustrated in FIG. 3 will be discussed in conjunction with FIGS. 4-12. The method of FIG. 3 can be implemented on a photolithography machine. An example of such machine is the Karl Suss MA6 Mask Aligner. However, other photolithography machines may be used to implement the method of FIG. 3.

Figure 4A:
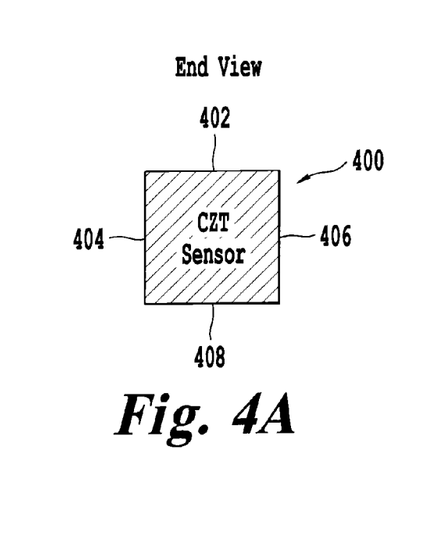
Figure 4B:
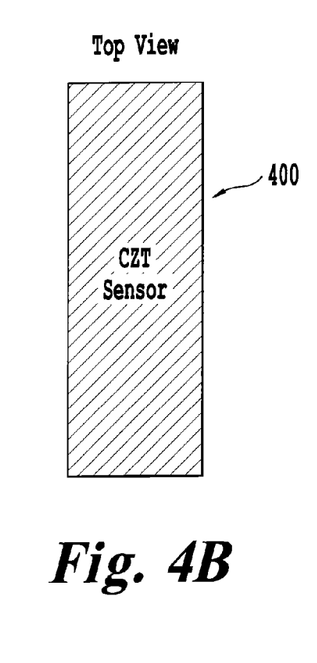
Figure 4C:
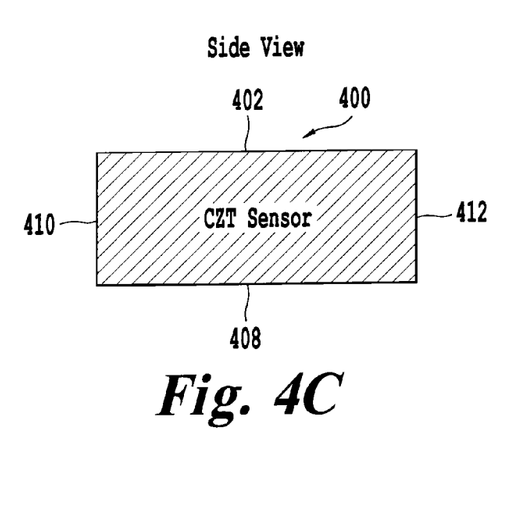

FIGS. 4A, 4B, and 4C illustrate the end view, top view, and side view, respectively, of the pixelated CZT sensor (with electrodes) 400. The different sides of the CZT sensor 400 are represented by 402-412, as illustrated in FIGS. 4A, 4B, and 4C.

In the first step of manufacturing the collimator structure (step 310 of FIG. 3), a first layer of SU-8 resist 500 is applied to the CZT sensor 400, as shown in FIGS. 4A, 4B, and 4C. As can be seen in the figures, in one embodiment, the layer of SU-8 resist 500 is half the height of the CZT sensor 400. However, the layer of SU-8 resist 500 can be of a different height with respect to the CZT sensor 400.

The height of the layer of SU-8 resist 500 is determined by how much height of the PCD is needed to be covered by the metal layer (for example, the thick layer of metal 900 discussed below). Whatever is not covered by SU-8 will be covered by metal overhang. Sometimes it is desirable to cover part of the PCD side surface by metal since the detector behavior is different and can be difficult to predict when X-rays enter from the side. This depends mainly on the quality of the sensor material and the imaging task.

Figure 5A:
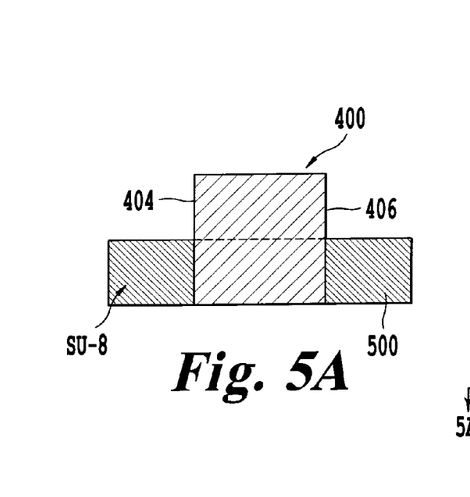
FIGS. 5A, 5B, 5C, 6A, 6B, 6C, 7A, 7B, 7C, 8A, 8B, 8C, 9A, 9B, 9C, 10A, 10B, 11A, 11B, 11C, 12A, 12B, and 12C illustrate the stages of fabrication of the collimator structure.
Figure 5B:
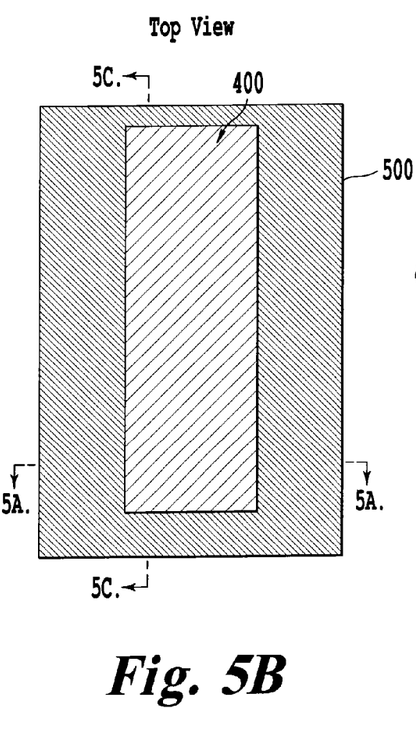
Figure 5C:
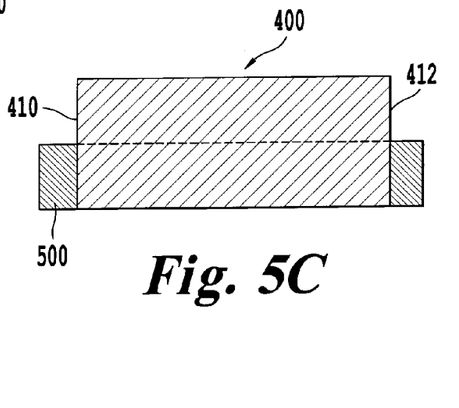
Figure 6A:
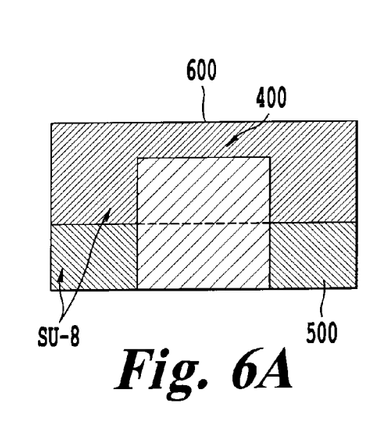
Figure 6B:
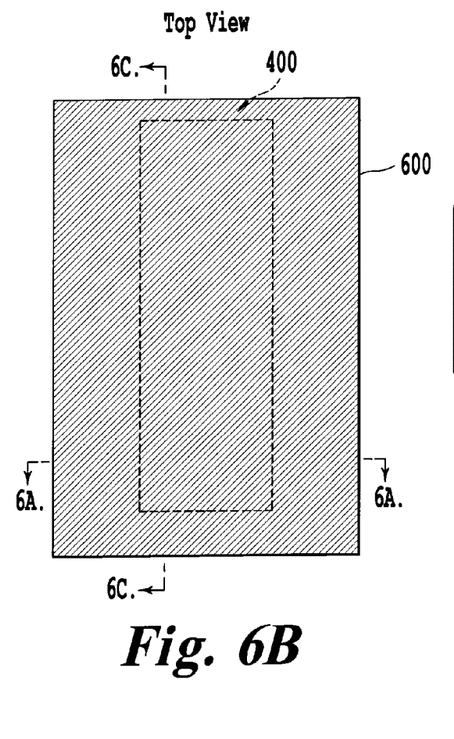
Figure 6C:
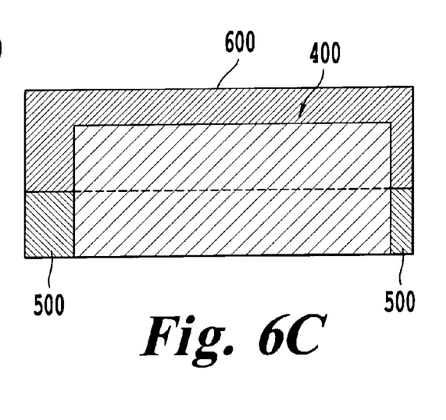

Next, flood exposure by ultraviolet (UV) light is performed on the structure shown in FIG. 5, at step 320, and then the structure is developed, at step 325, and cured, at step 330. After the structure is cured, a second layer of SU-8 resist 600 is applied, at step 340, over the first layer of SU-8 resist 500 and the CZT sensor 400, as shown in FIG. 6. As illustrated in FIG. 6, the second layer of SU-8 resist 600 covers the CZT sensor 400 on all sides (402, 404, 406, 410, and 412), except for the bottom side 408 of the CZT sensor 400. Although in the top view shown in FIG. 6B, it appears that the CZT sensor 400 is exposed, the second layer of SU-8 resist 600 in fact covers the top of the CZT sensor 400.

Figure 7A:
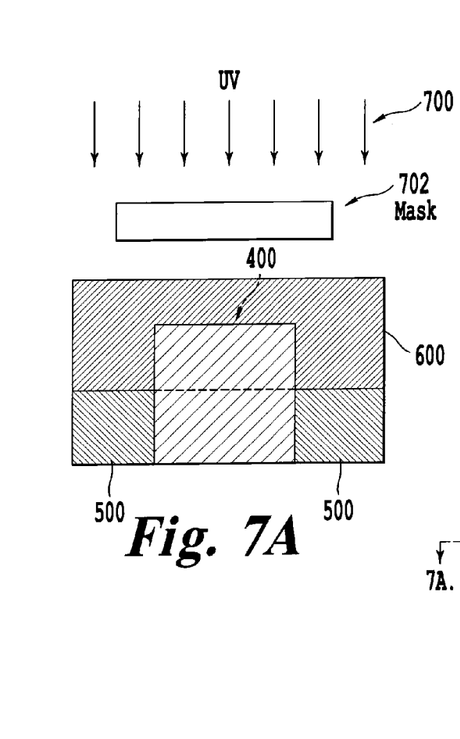
Figure 7B:
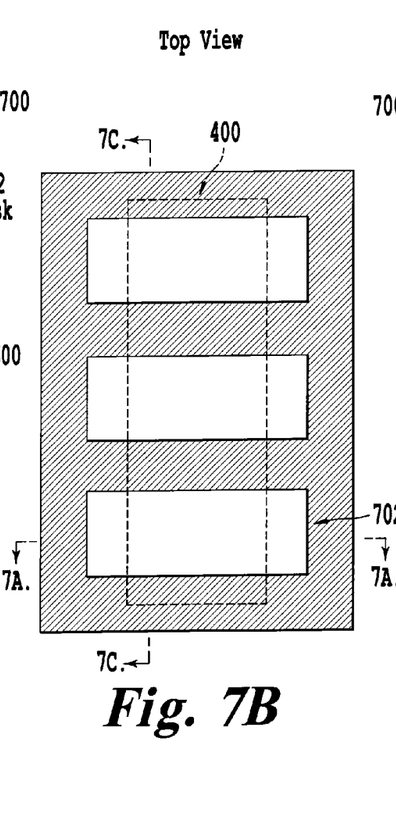
Figure 7C:
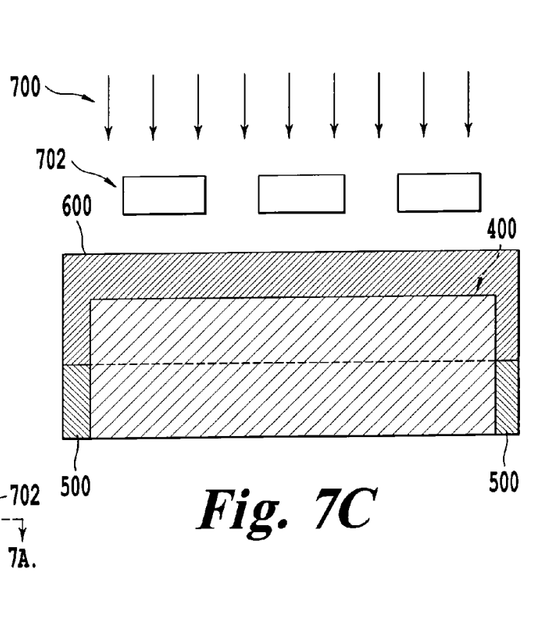

Next, at step 350, the fabrication method continues by exposing the structure to UV light 700 with photomask 702 in order to define a pattern, as shown in FIG. 7. In other words, the second layer SU-8 resist 600 is exposed to UV light to transfer the pattern from the photomask. A photomask (such as photomask 702) is a plate with holes or transparencies that allow the UV light 700 to shine through in a defined pattern.

Figure 8A:
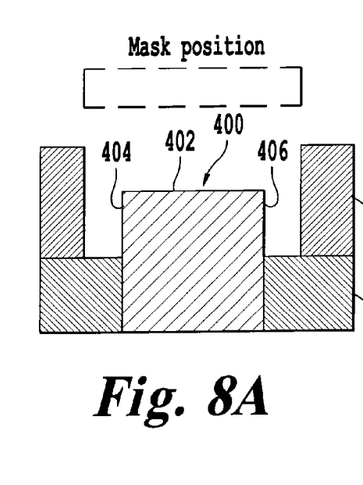

As can be seen in FIG. 8 and as discussed in step 360, portions of the second layer SU-8 resist 600 of the structure shown in FIG. 7 are developed (removed/washed), resulting in portions of the second layer SU-8 resist 600 being removed from the structure, thereby forming openings or gaps. The portions of the second layer SU-8 resist 600 are removed by a special solution or "developer." With an SU-8 resist, portions directly exposed to UV light will not be washed away and will be cured and stay. Such portions can be seen, for example, in FIG. 8A, as the portions outside (to the left and to the right) of the "mask position." However, for other types of photoresist, portions directly exposed to UV light will be washed away. For example, with positive-tone photoresists, regions exposed to light will be washed away, while the other regions will stay. With negative-tone photoresists, regions exposed to light will stay, while the other regions will be washed away. The method of FIG. 3 can use either a positive-tone photoresist or a negative-tone photoresist.

Figures 8B, 8C:
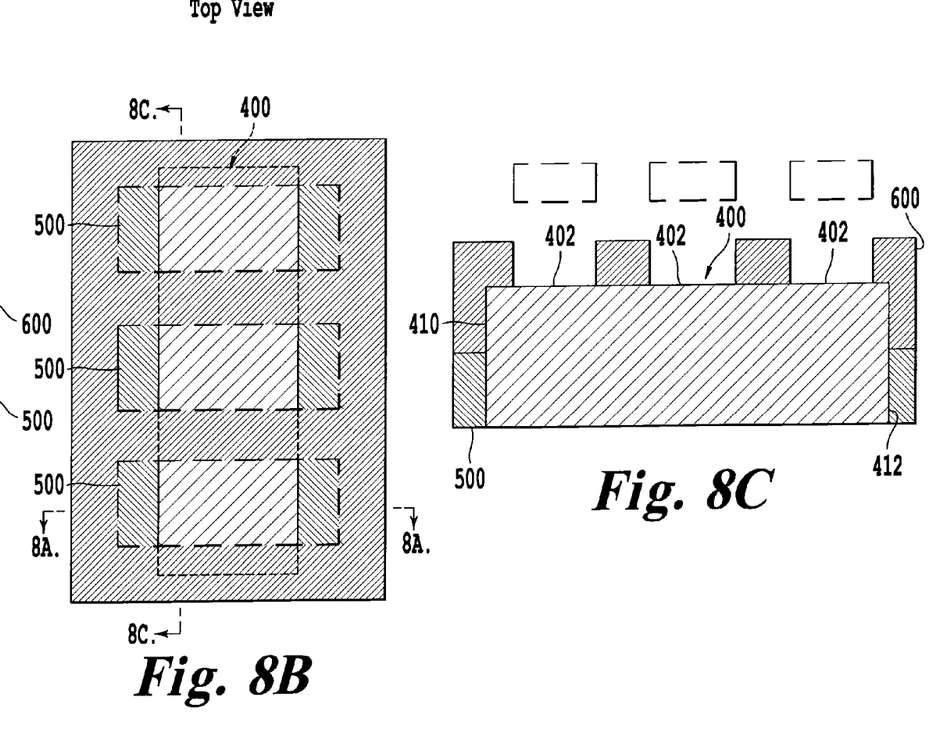

As a result of this step, as illustrated in FIGS. 8A, 8B, and 8C, portions of the CZT sensor 400 are entirely exposed at side (top) 402 and partially exposed around side 404 and side 406. On the other hand, as shown in FIG. 8C, sides 410 and 412 of the CZT sensor 400 are surrounded by the first layer of SU-8 resist 500 and the second layer of SU-8 resist 600, and thus are not exposed. After the second layer SU-8 resist 600 of the structure shown in FIG. 7 is developed (washed), the resultant structure (shown in FIG. 8) is cured, at step 370.

Figure 9A:
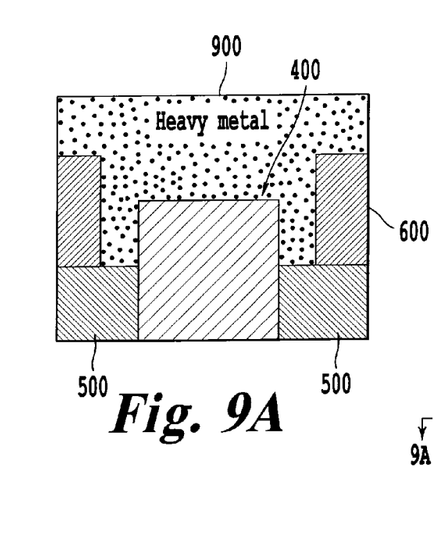
Figure 9B:
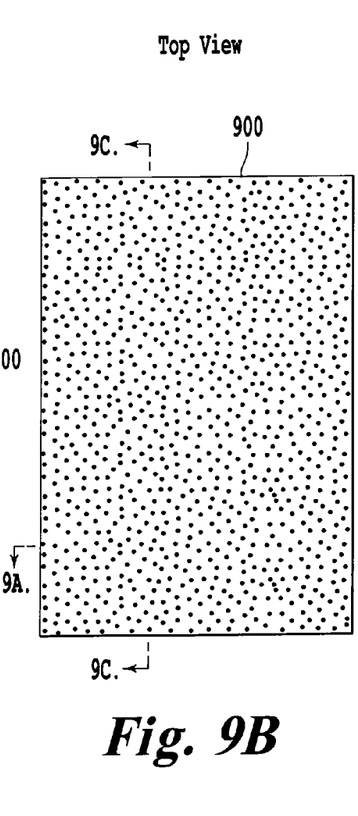
Figure 9C:
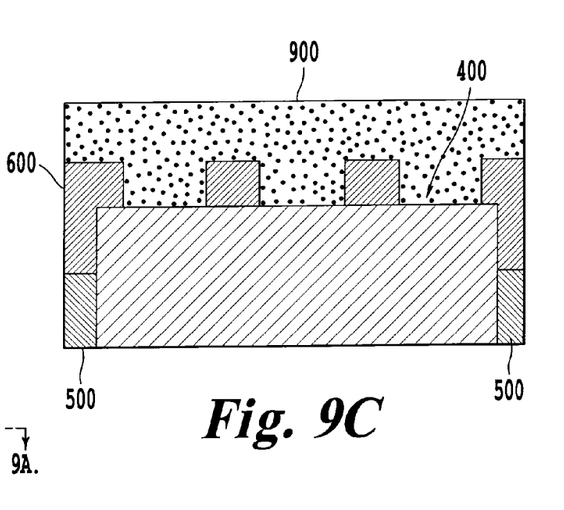

At step 380, in one embodiment of the method of fabrication, one thick layer of metal (of Pb or W) 900 is deposited (using sputter deposition, which is a physical vapour deposition method of depositing thin films by sputtering) on the structure of FIG. 8 to obtain the structure shown in FIG. 9. As illustrated in FIG. 9, the exposed portions shown in FIG. 8 are now covered with the thick layer of metal 900. In other words, the thick layer of metal 900 is introduced in the openings/gaps shown in FIG. 8. Also, from the top view shown in FIG. 9B, only the thick layer of metal 900 is visible.

The thickness of the thick layer of metal 900 need not be controlled as it will eventually be removed via polishing (as discussed below). However, it is not desirable for the thick layer of metal 900 to be too thick, as is increases the overall dimension, volume, and weight of the detector. The thick layer of metal 900 needs to be of a sufficient thickness to cover the structure. Ways to control the thickness include, for example, controlling the sputtering/evaporation rate of the metal during deposition and the duration thereof. In one embodiment, the thick layer of metal 900 has margins for later machining or polishing.

Figure 10A:
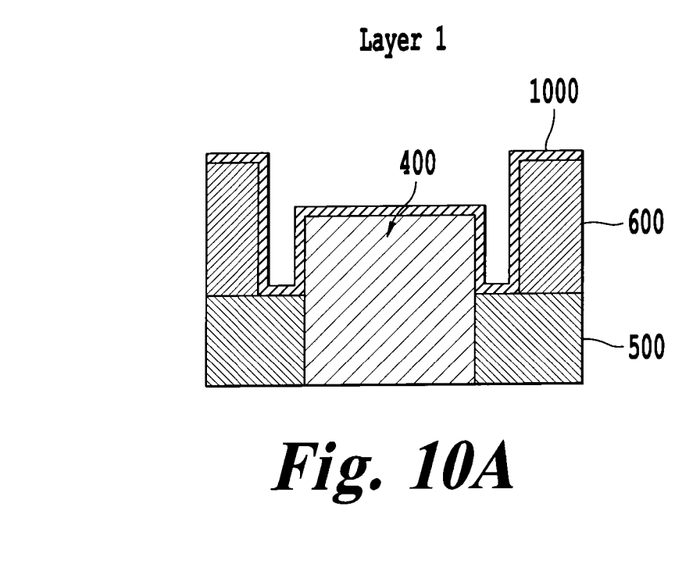
Figure 10B:
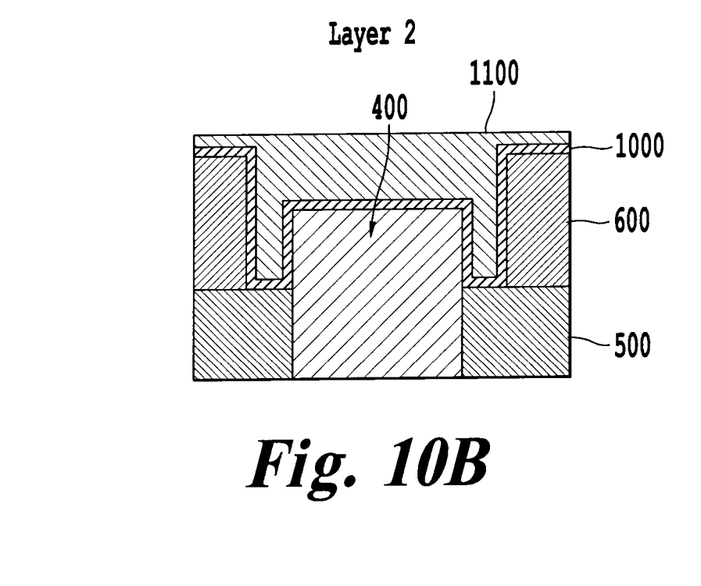

At step 380, in one embodiment of the method of fabrication, instead of depositing the thick layer of metal 900 as shown in FIG. 9, multiple layers of different metals are deposited. FIGS. 10A and 10B both show an end view of the collimator structure. FIG. 10A shows the depositing of a first metal layer 1000 on the structure of FIG. 8. The edges and corners may be filled by tilting the sputtering angle. FIG. 10B shows the depositing of a second metal layer 1100 on the structure of FIG. 10A. In other words, the second metal layer 1100 is deposited on the first metal layer 1000.

In the multiple metal layer design of FIG. 10, the second metal layer 1100 is of higher attenuation, while the first metal layer 1000 is of lower attenuation. Further, the first metal layer 1000 absorbs secondary irradiation from the second metal layer 1100 to prevent the first metal layer 1000 from contaminating CZT signals.

FIGS. 11 and 12 illustrate various structures with only one metal layer (for example, the thick layer of metal 900 of FIG. 9). It should be understood that, in some embodiments, the processes of FIGS. 11 and 12 can be performed with the multiple layers of different metals (the first metal layer 1000 and the second metal layer 1100 of FIG. 10).

Figures 11A, 11B:
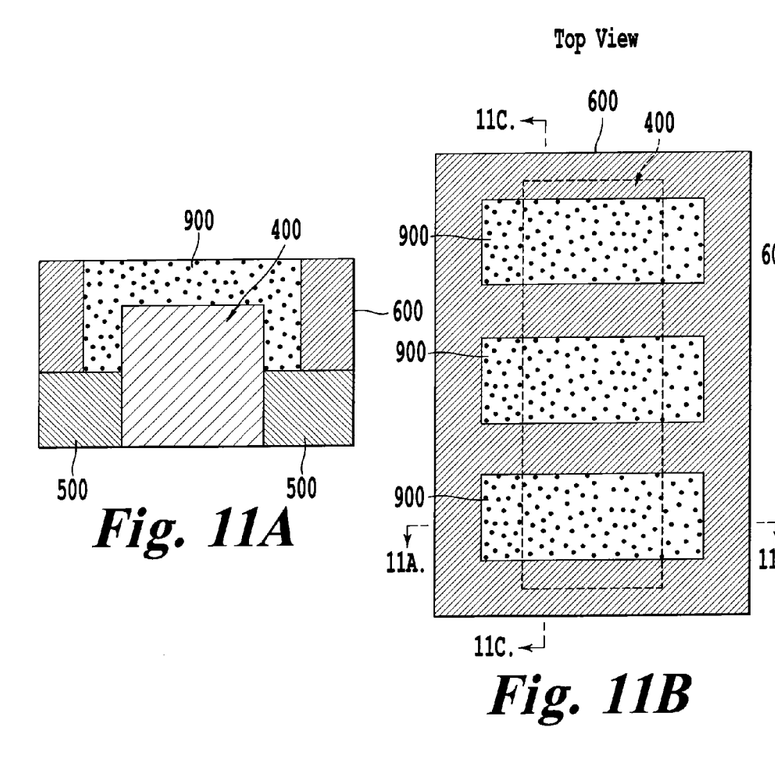
Figure 11C:
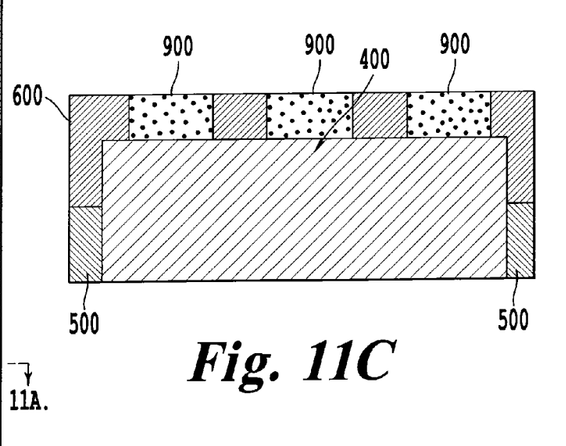

In FIG. 11, the method of fabrication continues in step 390 by polishing the top to remove excess metal layer of the thick layer of metal 900 (compare FIG. 9 with FIG. 11). As a result of the polishing, the thick layer of metal 900 is flush with the second layer of SU-8 resist 600, as can be seen in FIGS. 11A and 11C.

Figure 12A:
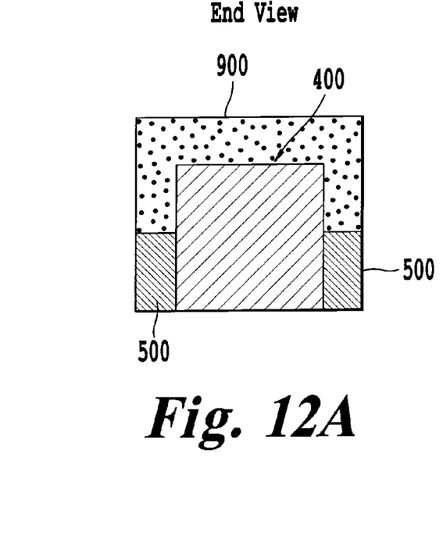
Figure 12B:
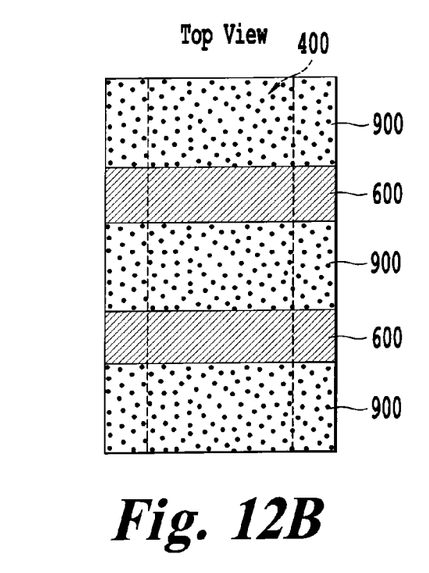
Figure 12C:
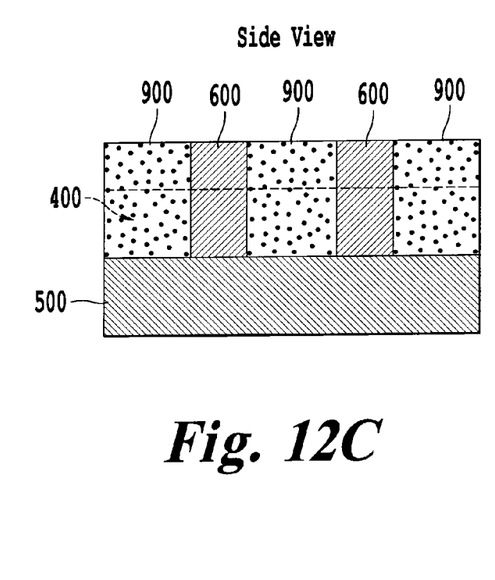

Finally, at step 395, dicing is performed to remove extra material along the sides of the structure of FIG. 11. FIG. 12 shows the final product resulting from the method of fabrication. As illustrated in FIGS. 12A, 12B, and 12C, parts of the first layer of SU-8 resist 500 and parts of the second layer of SU-8 600 are removed (compare FIG. 11 with FIG. 12). For example, in FIG. 12A, the first layer of SU-8 resist 500 remains, while in FIGS. 12B and 12C, the second layer of SU-8 resist 600 remains. Determining how much of the materials to dice is based on the dimension specification of the final sensor. Dicing should not be performed into the CZT sensor 400, and should be performed in such a way as to leave some residual SU-8 resist 500 to cover portions of CZT sensor 400, as shown in, for example, FIG. 12.

The sizes of each of the layers are determined based on the purpose of each layer and the imaging task. For example, for the thick layer of metal 900, the width determines the opening of the underneath PCD that exposes the PCD to radiation. Thus, the layer of metal 900 should collimate out enough radiation for the PCD to function, and its length should follow the PCD width dimension plus enough for overhang or edge margins. The thickness of the layer of metal 900 determines how much X-ray it stops. As an example, if the collimator is required to block out 99% of X-rays, then the layer of metal 900 should be of a thickness enough to achieve 99% stopping power.

Compared to traditional machining methods (such as, for example, Electric Discharge Machining (EDM)), the method discussed herein allows for mass production of many sensors in parallel, and finer control of dimensions in terms of precision and uniformity. In addition, the method discussed herein enables multi-layer metal deposition, which is not possible with, for example, EDM. Finally, the method discussed herein also integrates CZT material protection and the collimator fabrication in one process.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method of fabrication of a collimator structure on a detector of a Computed Tomography (CT) apparatus, the method comprising:
applying a first layer of resist to a semiconductor sensor;
applying a second layer of resist over the first layer of resist and the semiconductor sensor to cover both the first layer of resist and the semiconductor sensor;
exposing the second layer of resist to ultraviolet (UV) light with a photomask to transfer a pattern from the photomask to the second layer of resist;
removing portions of the second layer of resist corresponding to the pattern from the photomask to produce openings in the second layer of resist, which expose upper portions of the semiconductor sensor;
depositing a layer of metal in the openings and on the second layer of resist to cover the openings, the first layer of resist, the second layer of resist, and the semiconductor sensor;
polishing an upper portion of the layer of metal such that the layer of metal in the openings is flush with the second layer of resist; and
dicing the first layer of resist and the second layer of resist.

2. The method of claim 1, wherein
the depositing step includes depositing a second layer of metal to cover the layer of metal.

3. The method of claim 2, wherein
the layer of metal is of a lower attenuation than the second layer of metal.

4. The method of claim 1, wherein
the layer of metal is of one of lead (Pb), tungsten (W), and molybdenum (Mo).

5. The method of claim 1, wherein
the first layer of resist is an SU-8 resist.

6. The method of claim 1, wherein
the second layer of resist is an SU-8 resist.

7. The method of claim 1, further comprising:
performing flood exposure of the first layer of resist, before the applying of the second layer of resist.

8. The method of claim 7, further comprising:
curing the first layer of resist, after the performing of the flood exposure and before the applying of the second layer of resist.

9. The method of claim 1, further comprising:
curing the first layer of resist and the second layer of resist, after the removing of the portions of the second layer of resist.

10. The method of claim 1, wherein the semiconductor sensor is one of a cadmium zinc telluride (CZT) sensor, a cadmium telluride (CdTe) sensor, and a mercury iodide (HgI) sensor.

* * * * *